United States Patent [19]

Hansenne et al.

[11] Patent Number: 6,051,211

[45] Date of Patent: Apr. 18, 2000

[54] STABLE W/O PHOTOPROTECTIVE COSMETIC EMULSIONS

[75] Inventors: Isabelle Hansenne, Paris; Karine De Chabannes, Orleans, both of France

[73] Assignee: Societe L'Oreal S.A., Paris, France

[21] Appl. No.: 09/020,042

[22] Filed: Feb. 6, 1998

[30] Foreign Application Priority Data

Feb. 6, 1997 [FR] France ................................ 97 01367

[51] Int. Cl.⁷ .................................................. C03C 3/118
[52] U.S. Cl. .............................................. 424/59; 424/401
[58] Field of Search ...................... 244/59, 401; 514/63, 514/938

[56] References Cited

U.S. PATENT DOCUMENTS

| | | | |
|---|---|---|---|
| 4,145,413 | 3/1979 | Usdin et al. | 424/63 |
| 5,545,399 | 8/1996 | Lee et al. | 424/59 |
| 5,549,887 | 8/1996 | Galleguillos et al. | 424/66 |
| 5,989,529 | 11/1999 | Kaplan . | |

FOREIGN PATENT DOCUMENTS

| | | |
|---|---|---|
| 0590601 | 4/1994 | European Pat. Off. . |
| 0633018 | 1/1995 | European Pat. Off. . |
| 4420516 | 12/1995 | Germany . |

*Primary Examiner*—Thurman K. Page
*Assistant Examiner*—Alysia Berman
*Attorney, Agent, or Firm*—Burns, Doane, Swecker & Mathis, L.L.P.

[57] ABSTRACT

Stable, water-resistant photoprotective water-in-oil cosmetic emulsions, well suited for the photoprotection of human skin and/or hair against the deleterious effects of UV irradiation, comprise an effective stabilizing/emulsifying amount of a pair of active emulsifying agents, said emulsifying agent pair comprising (i) at least one polyalkylpolyethersiloxane emulsifier substituted by polyoxyethylene and polyoxypropylene moieties grafted onto the backbone polymer thereof, and (ii) at least one water-in-oil emulsifying polyoxyalkylenated glycol fatty acid ester polymer.

23 Claims, No Drawings

STABLE W/O PHOTOPROTECTIVE COSMETIC EMULSIONS

CROSS-REFERENCE TO PRIORITY APPLICATION

This application claims priority under 35 U.S.C. §119 of FR-01367, filed Feb. 6, 1997, hereby expressly incorporated by reference.

BACKGROUND OF THE INVENTION

1. Technical Field of the Invention

The present invention relates to novel water-in-oil emulsions, in particular to novel cosmetic compositions comprised thereof for the photoprotection of the skin and/or hair against the damaging effects of UV radiation, and which comprise the combination of two judiciously selected emulsifying agents.

2. Description of the Prior Art

It is known to this art that light radiation of wavelengths ranging from 280 nm to 400 nm promotes tanning of human skin and that radiation of wavelengths ranging from 280 nm to 320 nm, i.e., UV-B irradiation, causes erythemas and skin burns which can impair the development of a natural tan and/or bronzing. For these reasons and also for aesthetic reasons, continuous need exists for means for controlling such natural tanning/bronzing and, thus, for controlling the coloration of the skin. Hence, such UV-B radiation must be screened from the skin.

It is also known to this art that UV-A radiation, of wavelengths ranging from 320 nm to 400 nm, which causes the skin to tan, also adversely affects it, especially in the case of sensitive skin or skin which is continually exposed to solar radiation. In particular, UV-A radiation causes a loss of skin elasticity and the appearance of wrinkles, promoting premature skin aging. Such irradiation promotes the triggering of the erythemal reaction or accentuates this reaction in certain individuals and may even be the source of phototoxic or photoallergic reactions. Thus, for aesthetic and cosmetic reasons, such as preservation of the natural elasticity of the skin, for example, more and more subjects wish to control the effect of UV-A radiation on their skin. It is thus desirable to also screen out the UV-A radiation.

A wide variety of cosmetic and/or dermatological compositions for the photoprotection (UV-A and/or UV-B) of human skin are known to this art.

These photoprotective/sunscreen compositions are quite typically oil-in-water emulsions, namely, a cosmetically and/or dermatologically acceptable vehicle, diluent or carrier comprising a continuous aqueous dispersing phase and a discontinuous oily dispersed phase, due, in particular, to their pleasant feel (similar to water) and to their formulation as non-greasy milks or creams.

However, one of the disadvantages of oil-in-water emulsions is that they very easily lose their effectiveness with respect to UV protection as soon as they come into contact with water; this because the screening agents which they contain in their aqueous phase are removed by the water, during bathing in the sea or in swimming pools, for example, or, alternatively, under the shower or when playing water sports, and the overall photoprotective power of these compositions thus is greatly reduced.

Accordingly, in certain instances where a particularly high and lasting protection is desired, as for childrens' skin or for sensitive skin, it is preferable to employ water-in-oil compositions which exhibit good water persistence and which thus retain a very good photoprotective power even after bathing several times.

For such skin types, there is, in addition, a desire to minimize the risk of sensitization while avoiding, as far as possible, the presence within the formulations of active agents capable of causing skin reactions. Thus, need continues to exist for compositions which are simultaneously free of preservatives, while exhibiting an optimum stability which is maintained throughout the time of storage and ultimate use of the products.

Lastly, as these compositions are intended, in particular, to be topically applied onto the skin, they should also exhibit good cosmetic properties, namely, a good appearance, a good resistance to the immediate environment and, in the specific case of sunscreen compositions for children, non-adherence to sand, with which they are often in contact (beaches, play areas). These compositions should also spread easily and be pleasant in appearance.

Emulsions of water-in-oil type stabilized by silicone emulsifiers, such as dimethicone copolyols, which are well known for their good water-in-oil emulsifying properties, are known and are described, for example, in GB-2,242,358.

SUMMARY OF THE INVENTION

It has now surprisingly been determined that novel photoprotective/sunscreen compositions comprising the pair of at least one polyalkylpolyethersiloxane judiciously selected from among the silicone emulsifiers, and a specific polymer exhibiting water-in-oil emulsifying properties provide water-in-oil emulsions having improved stability.

Briefly, the present invention features novel stabilized emulsions of water-in-oil type, comprising at least one particular silicone emulsifier, namely, a polyalkylpolyethersiloxane substituted by polyoxyethylene and polyoxypropylene chains grafted onto the backbone polymer chain, and at least one polymer of the polyoxyalkylenated glycol fatty acid ester type having water-in-oil emulsifying properties.

DETAILED DESCRIPTION OF BEST MODE AND SPECIFIC/PREFERRED EMBODIMENTS OF THE INVENTION

More particularly according to the present invention, the subject emulsions present the advantages of being persistent with respect to water, or water-resistant, and of being particularly stable over time, even without a preservative.

Moreover, the emulsions in accordance with the invention exhibit very little adherence to sand and exhibit very good cosmetic properties.

The present invention thus features the emulsions described above, and the formulation therefrom of cosmetic and/or dermatological compositions for the protection of the skin and/or hair against ultraviolet radiation.

Too, this invention features a cosmetic treatment, regime or regimen for the protection of the skin and/or hair against ultraviolet radiation, which essentially comprises topically applying thereto an effective sunscreen amount of a cosmetic and/or dermatological composition or emulsion as described above.

An essential characteristic of the compositions in accordance with this invention is that they comprise a specific silicone emulsifier comprising a polyalkylpolyethersiloxane bearing polyoxyethylene and polyoxypropylene chains grafted onto the backbone polymer chain.

Such silicone emulsifier is advantageously selected from among the compounds of the following general formula (I):

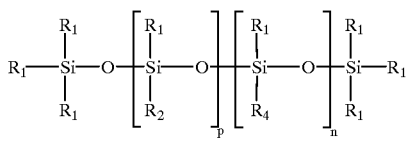

in which $R_1$ and $R_4$, which may be identical or different, are each a hydrogen atom, a linear or branched $C_1$–$C_{30}$ alkyl radical, or a phenyl radical; the radicals $R_2$, which may be identical or different, are each a radical —$(C_xH_{2x})$—$(OC_2H_4)_a$—$(OC_3H_6)_b$—$OR_3$, wherein the radicals $R_3$, which may be identical or different, are each a hydrogen atom, a linear or branched alkyl radical having from 1 to 12 carbon atoms or a linear or branched acyl radical having from 2 to 12 carbon atoms; n ranges from 1 to 1,000; p ranges from 1 to 30; a ranges from 1 to 50; b ranges from 1 to 50; and x ranges from 1 to 5.

The number-average molecular weight of this silicone emulsifier is advantageously greater than or equal to 15,000 and preferably ranges from 20,000 to 40,000.

A first class of polyalkylpolyethersiloxanes particularly well suited for formulation into the compositions according to the invention is that of the compounds having the above formula (I) in which the $R_1$ and $R_4$ radicals are identical and each is a methyl radical and the $R_3$ radical is a hydrogen atom.

Exemplary silicone emulsifiers of this class include the polydimethyl/oxyethylenated oxypropylenated (EO/PO 18/18) methylsiloxane in which n is 396 and p is 4, with a number-average molecular weight of greater than 30,000 (CTFA name: Cyclomethicone 90% Dimethicone copolyol 10%), marketed under the trademark of "Silicone $Q_2$3225C" by Dow Corning.

In the above description and in that to follow, "EO" represents one mole of ethylene oxide and "PO" represents one mole of propylene oxide.

A second class of polyalkylpolyethersiloxanes particularly well suited for formulation into the compositions according to the invention is that of the compounds having the above formula (I) in which the $R_1$ radicals are each a methyl radical and the $R_4$ radicals are each a lauryl radical.

A particularly preferred silicone emulsifier of this second class is the polymethyllauryl/oxyethylenated oxypropylenated (EO/PO 18/18) methylsiloxane in which n is 35 and p is 3, with a number-average molecular weight of greater than 25,000 (CTFA name: Laurylmethicone copolyol 91%, Isostearyl alcohol 9%), marketed under the trademark "DC Q2-5200" by Dow Corning.

The silicone emulsifier or emulsifiers are generally present in the compositions according to the invention in a proportion of active material ranging from 0.2% to 5% by weight, preferably from 0.25% to 3% by weight, with respect to the total weight of the composition.

A second essential compound formulated into the compositions according to the invention is a polymer of the polyoxyalkylenated glycol fatty acid ester type having water-in-oil emulsifying properties.

The fatty acid ester of said polymer is preferably polyhydroxylated. In particular, this polymer is a block polymer, preferably of ABA structure, containing poly(hydroxylated ester) blocks and polyethylene glycol blocks.

The fatty acid ester of said emulsifying polymer as described above generally includes a chain containing from 12 to 20 carbon atoms, preferably from 14 to 18 carbon atoms. The esters are advantageously oleates, palmitates or stearates.

The polyethylene glycol blocks of such emulsifying polymers as described above preferably comprise from 4 to 50 mol of ethylene oxide and more preferably from 20 to 40 mol of ethylene oxide.

One material which is particularly suitable for the formulation of the compositions of the invention is polyethylene glycol dipolyhydroxystearate, in which the polyethylene glycol contains 30 EO units, marketed under the trademark "Arlacel P 135" by ICI.

The polymer of the polyoxyalkylenated glycol fatty acid ester type is generally present in the compositions according to the invention at a content which can range from 0.2% to 10% by weight with respect to the total weight of the composition and preferably from 0.25% to 5% by weight with respect to the total weight of the composition.

The compositions of this invention also comprise an oily phase which can contain one or more fatty substances, and such fatty substances may comprise an oil or a wax or mixture thereof. By "oil" is intended a compound which is liquid at room temperature. By "wax" is intended a compound which is solid or substantially solid at room temperature and which has a melting point generally above 35° C.

Exemplary oils include the mineral oils (petrolatum), vegetable oils (sweet almond, macadamia, grape seed or jojoba oil), synthetic oils, such as perhydrosqualene, fatty alcohols, acids or esters (such as the benzoate of $C_{12}$–$C_{15}$ alcohols marketed under the trademark "Finsolv TN" by Finetex, octyl palmitate, isopropyl lanolate or triglycerides, including those of capric/caprylic acids), oxyethylenated or oxypropylenated fatty esters and ethers, fluorinated oils or alternatively polyalkylenes, such as polydecene.

And exemplary waxy compounds include paraffin, carnauba wax, beeswax or hydrogenated castor oil.

The oily phase can also comprise a volatile or non-volatile silicone oil, such as cyclomethicones or dimethicones. For example, it is possible to formulate into the compositions of the present invention, a volatile silicone oil such as, for example, the cyclomethicones marketed under the trademarks "DC 245 Fluid" or "DC 246 Fluid" by Dow Corning.

The cosmetic and/or dermatological compositions according to the present invention can, of course, contain one or more hydrophilic or lipophilic sunscreen agents which are active in the UVA and/or UVB range (absorbers). These screening agents are advantageously selected from among cinnamic derivatives, salicylic derivatives, dibenzoylmethane derivatives, benzylidenecamphor derivatives, benzimidazole derivatives, triazine derivatives, benzophenone derivatives, $\beta,\beta'$-diphenylacrylate derivatives, p-aminobenzoic acid derivatives, or the screening polymers and screening silicones described in WO-93/04665. Other suitable organic screening agents are described in EP-A-0, 487,404.

The cosmetic and/or dermatological compositions of this invention can also contain coated or uncoated metal oxide pigments or alternatively nanopigments (mean size of the primary particles: generally ranging from 5 nm to 100 nm, preferably from 10 to 50 nm), such as, for example, titanium dioxide (amorphous or crystallized in the rutile and/or anatase state), iron oxide, zinc oxide, zirconium oxide or cerium oxide nanopigments, which are all photoprotective agents per se well known to this art which act by physically blocking (reflection and/or scattering) UV radiation. Conventional coating agents include, moreover, alumina and/or aluminum stearate or silicones. Such coated or uncoated metal oxide nanopigments are, in particular, described in EP-A-0,518,772 and EP-A-0,518,773.

The nanopigments are advantageously present in the final compositions according to the invention in an amount ranging from 0.1% to 20%, preferably from 0.2% to 10%, by weight with respect to the total weight of the composition.

The compositions according to the invention can also contain thickeners which can be selected, in particular, from among the crosslinked polyacrylic acids, polyacrylic acids bearing a fatty chain substituent, or modified or unmodified guar gums and celluloses, such as hydroxypropylated guar gum, methylhydroxyethylcellulose and hydroxypropylmethylcellulose.

The compositions according to the invention can also contain agents for the artificial tanning and/or browning of the skin (self-tanning agents), such as, for example, dihydroxyacetone (DHA).

The compositions of this invention can, in addition, comprise conventional cosmetic and/or dermatological adjuvants and additives selected, in particular, from among the organic solvents, softeners, antioxidants, agents for combating free radicals, opacifying agents, stabilizers, emollients, α-hydroxy acids, antifoaming agents, moisturizing agents, vitamins, fragrances, preservatives, surfactants, fillers, sequestering agents, polymers, propellants, basifying or acidifying agents, dyes, colorants, or any other ingredient typically employed in the cosmetic and/or dermatological field, in particular for the formulation of sunscreen compositions as emulsions.

Indeed, one skilled in this art will take care to select the optional additional compound or compounds indicated above and/or their amounts such that the advantageous properties intrinsically provided by the binary combination in accordance with the present invention are not, or not substantially, detrimentally affected by the envisaged addition or additions.

The compositions according to the invention can be formulated according to techniques for the preparation of emulsions of water-in-oil type which are well known to this art.

The cosmetic and/or dermatological compositions of the invention can be used as photoprotective compositions for the human epidermis or the hair against ultraviolet radiation, as sunscreen compositions or as makeup products.

Thus, this invention features the combination of the polyalkylpolyethersiloxanes bearing polyoxyethylene and polyoxypropylene moieties grafted onto the backbones thereof and polymers of the polyoxyalkylenated glycol fatty acid ester type, having water-in-oil emulsifying properties as described above and constituting water-in-oil emulsifying systems, in particular for the formulation of cosmetic and/or dermatological compositions.

In order to further illustrate the present invention and the advantages thereof, the following specific examples are given, it being understood that same are intended only as illustrative and in nowise limitative.

EXAMPLE 1

Comparative tests were carried out in order to demonstrate the judicious selection of the present invention from among water-in-oil silicone emulsifiers known to the prior art, in particular as regards the necessary substitution, onto the backbone chains of the polyalkylsiloxanes, of oxyethylenated and oxypropylenated groups.

The formulations A to E comprising the following common vehicle, diluent or carrier were formulated (the amounts are expressed as percentage by weight with respect to the total weight of the composition):

| | |
|---|---|
| (a) polyalkylsiloxane | 2% |
| (b) polyethylene glycol (30 EO) dipolyhydroxystearate, marketed under the trademark "Arlacel P 135" by ICI | 2% |
| (c) benzoate of $C_{12}/C_{15}$ alcohols, marketed under the trademark "Finsolv TN" by Finetex | 6% |
| (d) silicone oil | 16% |
| (e) UV screening system | 12% |
| (f) titanium dioxide | 3% |
| (g) sodium chloride | 1% |
| (h) glycerol | 4% |
| (i) sequestering agent | 0.3% |
| (j) preservatives | q.s. |
| (k) water | q.s. for 100% | with the exception of the composition B in which the silicone oil (16%) had not been added, by reason of the fact that the commercial product comprising the polyalkylsiloxane ("DC 3225 C", cf. Table I below) also contained a silicone oil (cyclomethicone).

The respective polyalkylsiloxane compositions in the formulae A to E are reported in the following Table I (the amounts below correspond to the percentage of commercial product necessary in order to provide 1.8% of active material as percentage by weight with respect to the total weight of the composition):

TABLE I

| Formula | Silicone | Level |
|---|---|---|
| A | "DC Q2-5200" | 2% |
| B | "DC 3225 C" | 18% |
| C | "Silwax WD-IS" | 1.8% |
| D | "DC 193" | 1.8% |
| E | "Fancorsil LIM-3" | 1.8% |

In the above Table I:
(i) "DC Q2-5200" is a polymethyllauryl/oxyethylenated oxypropylenated methylsiloxane (35/3) (EO/PO 18/18) (CTFA name: Laurylmethicone copolyol 91%, Isostearyl alcohol 9%) marketed by Dow Corning (emulsifier according to the invention).
(ii) "DC 3225 C" is a polydimethyl/oxyethylenated oxypropylenated methylsiloxane (396/4) (EO/PO 18/18) (CTFA name: Cyclomethicone 90% Dimethicone copolyol 10%) marketed by Dow Corning (emulsifier according to the invention).
(iii) "Silwax WD-IS" is an oxyethylenated polydimethylsiloxane containing isostearate groups (CTFA name: Dimethicone copolyol isostearate) marketed by Siltech (emulsifier not in accordance with the invention).
(iv) "DC 193" is an oxyethylenated polydimethylsiloxane (4/9) (12 EO) (CTFA name: Dimethicone copolyol) marketed by Dow Corning (emulsifier not in accordance with the invention).
(v) "Fancorsil LIM-3" is a polyoxyethylenated polydimethylsiloxane containing eicosanoate groups (CTFA name: Dimethicone copolyol eicosanoate) marketed by Fanning Corporation (emulsifier not in accordance with the invention).

Procedure:
The emulsions A to E were formulated using a Turbotest Rayneri paddle stirrer. The fatty phase containing, inter alia, the polyalkylsiloxane and the polyethylene glycol dipolyhydroxystearate was heated to 60° C. The aqueous phase was heated to 60° C. separately. The pigment was introduced with vigorous stirring into the fatty phase. The aqueous phase was subsequently incorporated gradually in the fatty phase, while continuing to stir vigorously. Finally, the emulsion obtained was permitted to cool, with moderate stirring, to room temperature.

For each of the emulsions thus prepared, three samples were stored, with light excluded, at room temperature, at 45° C. and at 55° C., respectively, for several days.

The preparation conditions and the stability results (in days (d) and hours (h)) are reported in the following Table II:

TABLE II

| Formula | Preparation | Stability at room temperature | Stability at 45° C. | Stability at 55° C. |
|---|---|---|---|---|
| A (invention) | easy | 15 d: good | 15 d: good | 15 d: good |
| B (invention) | easy | 15 d: good | 15 d: good | 15 d: good |
| C (comparative) | difficult | 7 d: unstable slimy appearance | 48 h: unstable | 48 h: unstable |
| D (comparative) | impossible | | | |
| E (comparative) | impossible | | | |

These results clearly indicate that the combination in accordance with the invention, namely, a polymer of the polyoxyalkylenated glycol fatty acid ester type having water-in-oil emulsifying properties and a silicone emulsifier comprised of a polyalkylpolyethersiloxane bearing polyoxyethylene and polyoxypropylene chains grafted onto the backbone chain thereof, provided good stability of the emulsions after storage for 15 days at 45° C., indeed at 55° C., in contrast to the emulsions of the prior art containing the same polyethylene glycol dipolyhydroxystearate in combination with a conventional silicone emulsifier.

EXAMPLE 2

One specific example of a sunscreen composition of water-in-oil type in accordance with the invention is as follows:

| | |
|---|---|
| (a) polymethyllauryl/oxyethylenated and oxypropylenated methylsiloxane (35/3) (18 EO/18 PO), marketed under the trademark "DC Q2-5200" by Dow Corning | 2% |
| (b) polyethylene glycol (30 EO) dipolyhydroxystearate, marketed under the trademark "Arlacel P 135" by ICI | 2% |
| (c) benzoate of $C_{12}/C_{15}$ alcohols, marketed under the trademark "Finsolv TN" by Finetex | 6% |
| (d) silicone oil | 16% |
| (e) 2-ethylhexyl α-cyano-β,β' diphenylacrylate, marketed under the trademark "Uvinul N 539" by BASF | 6% |
| (f) titanium dioxide | 3% |
| (g) sodium chloride | 1% |
| (h) glycerol | 4% |
| (i) sequestering agent | 0.3% |
| (j) preservatives | q.s. |
| (k) water | q.s. for 100% |

This composition was particularly stable under the storage conditions indicated in Example 1 and was also resistant to removal by water.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A stable, water-resistant photoprotective water-in-oil cosmetic emulsion which comprises an effective stabilizing/emulsifying amount of a pair of active emulsifying agents, said emulsifying agent pair comprising (i) at least one polyalkylpolyethersiloxane emulsifier substituted by polyoxyethylene and polyoxypropylene moieties grafted onto the backbone polymer thereof, and (ii) at least one water-in-oil emulsifying ABA block polymer containing poly (hydroxylated ester) blocks and polyethylene glycol blocks.

2. The photoprotective w/o cosmetic emulsion as defined by claim 1, formulated into a topically applicable, cosmetically acceptable vehicle, diluent or carrier therefor.

3. The photoprotective w/o cosmetic emulsion as defined by claim 1, the fatty acid ester moiety of said at least one polyoxyalkylenated polymer (ii) having from 12 to 20 carbon atoms.

4. The photoprotective w/o cosmetic emulsion as defined by claim 3, said at least one polyoxyalkylenated polymer (ii) having from 14 to 18 carbon atoms.

5. The photoprotective w/o cosmetic emulsion as defined by claim 1, said at least one fatty acid ester polymer (ii) comprising polyethylene glycol blocks containing from 4 to 50 mol of ethylene oxide.

6. The photoprotective w/o cosmetic emulsion as defined by claim 5, said at least one fatty acid ester polymer (ii) comprising polyethylene glycol blocks containing from 20 to 40 mol of ethylene oxide.

7. The photoprotective w/o cosmetic emulsion as defined by claim 1, said at least one fatty acid ester polymer (ii) comprising a polyethylene glycol dipolyhydroxystearate containing about 30 mol of ethylene oxide.

8. The photoprotective w/o cosmetic emulsion as defined by claim 1, said at least one polyalkylpolyethersiloxane (i) having the structural formula (I):

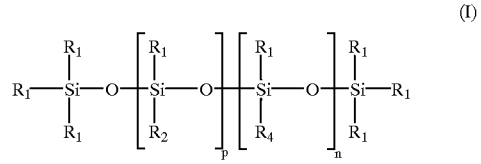

in which $R_1$ and $R_4$, which may be identical or different, are each a hydrogen atom, a linear or branched $C_1$–$C_{30}$ alkyl radical, or a phenyl radical; the radicals $R_2$, which may be identical or different, are each a radical $—(C_xH_{2x})—(OC_2H_4)_a—(OC_3H_6)_b—OR_3$, wherein the radicals $R_3$, which may be identical or different, are each a hydrogen atom, a linear or branched alkyl radical having from 1 to 12 carbon atoms or a linear or branched acyl radical having from 2 to 12 carbon atoms; n ranges from 1 to 1,000; p ranges from 1 to 30; a ranges from 1 to 50; b ranges from 1 to 50; and x ranges from 1 to 5.

9. The photoprotective w/o cosmetic emulsion as defined by claim 8, wherein formula (I) each radical $R_1$ and $R_4$ is a methyl radical and $R_3$ is hydrogen.

10. The photoprotective w/o cosmetic emulsion as defined by claim 9, wherein said polyalkyl polyether siloxane having structural formula (I) comprises at least one polydimethyl/oxyethylenated oxypropylenated methylsiloxane (i) having a number-average molecular weight of greater than 30,000 and where in formula (I) n is about 396, p is about 4, a is about 18 and b is also about 18.

11. The photoprotective w/o cosmetic emulsion as defined by claim 8, wherein formula (I) each radical $R_1$ is a methyl radical and each radical $R_4$ is a lauryl radical.

12. The photoprotective w/o cosmetic emulsion as defined by claim 11, wherein said polyalkyl polyether siloxane having structural formula (I) comprises at least one polymethyllauryl/oxyethylenated oxypropylenated methylsiloxane (i) having a number-average molecular weight of greater than 25,000 and where in formula (I) n is about 35, p is about 3, a is about 18 and b is also about 18.

13. The photoprotective w/o cosmetic emulsion as defined by claim 1, devoid of any preservative therefor.

14. The photoprotective w/o cosmetic emulsion as defined by claim 1, said at least one polyalkylpolyethersiloxane emulsifier (i) comprising from 0.2% to 5% by weight thereof.

15. The photoprotective w/o cosmetic emulsion as defined by claim 14, said at least one polyalkylpolyethersiloxane emulsifier (i) comprising from 0.25% to 3% by weight thereof.

16. The photoprotective w/o cosmetic emulsion as defined by claim 14, said at least one fatty acid ester polymer (ii) comprising from 0.2% to 10% by weight thereof.

17. The photoprotective w/o cosmetic emulsion as defined by claim 15, said at least one fatty acid ester polymer (ii) comprising from 0.25% to 5% by weight thereof.

18. The photoprotective w/o cosmetic emulsion as defined by claim 1, comprising an oil, wax, or mixture thereof.

19. The photoprotective w/o cosmetic emulsion as defined by claim 1, comprising at least one hydrophilic or lipophilic UVA, UVB sunscreen agent, or a combination thereof.

20. The photoprotective w/o cosmetic emulsion as defined by claim 1, comprising at least one mineral oxide pigment or nanopigment UV-photoprotective agent.

21. The photoprotective w/o cosmetic emulsion as defined by claim 1, comprising at least one cosmetic or an dermatological adjuvant and/or additive selected from among the organic solvents, softeners, antioxidants, agents for combating free radicals, opacifying agents, stabilizers, emollients, α-hydroxy acids, antifoaming agents, moisturizing agents, vitamins, fragrances, preservatives, surfactants, fillers, sequestering agents, polymers, propellants, basifying or acidifying agents, dyes, colorants, and other cosmetic and dermatological ingredient.

22. The photoprotective w/o cosmetic emulsion as defined by claim 1, comprising at least one active agent for the artificial tanning or browning of human skin.

23. A method for photoprotecting at least one of human skin or hair against the deleterious effects of ultraviolet irradiation, comprising topically applying thereto an effective amount of the protective w/o cosmetic emulsion as defined by claim 1.

* * * * *